United States Patent
Suzuki et al.

(10) Patent No.: US 6,821,120 B2
(45) Date of Patent: Nov. 23, 2004

(54) DENTAL HANDPIECE WITH TOOL HOLDER

(75) Inventors: Tetsuji Suzuki, Utsunomiya (JP); Yuichi Shibata, Kanuma (JP)

(73) Assignee: Nakanishi, Inc., Tochigi (JP)

( * ) Notice: Subject to any disclaimer, the term of this patent is extended or adjusted under 35 U.S.C. 154(b) by 0 days.

(21) Appl. No.: 10/153,396

(22) Filed: May 21, 2002

(65) Prior Publication Data

US 2002/0177101 A1 Nov. 28, 2002

(30) Foreign Application Priority Data

May 22, 2001 (JP) .................................... 2001-152160

(51) Int. Cl.$^7$ ............................................. A61C 1/14
(52) U.S. Cl. ...................................................... 433/129
(58) Field of Search ............................... 433/127, 128, 433/129

(56) References Cited

U.S. PATENT DOCUMENTS

| | | | |
|---|---|---|---|
| 3,171,664 A | 3/1965 | Benjamin | 279/50 |
| 3,942,392 A | * 3/1976 | Page, Jr. et al. | |
| 4,595,363 A | 6/1986 | Nakanishi | 433/129 |
| 4,611,990 A | * 9/1986 | Lares et al. | 433/129 |

FOREIGN PATENT DOCUMENTS

| | | | | |
|---|---|---|---|---|
| EP | 0 420 169 A1 | 4/1991 | | A61C/1/14 |
| JP | 47-29980 U | 4/1971 | | |
| JP | 58-185209 U | 6/1982 | | |
| JP | 60-55413 U | 9/1983 | | |
| JP | 1-250247 A | 10/1989 | | |
| JP | 3-165756 A | 7/1991 | | |
| JP | 61-30650 U | 5/1994 | | |
| JP | 11-56 U | 4/1999 | | |
| JP | 11-285503 A | 10/1999 | | |
| JP | 2001-152160 | 5/2001 | | |
| WO | WO 99 66854 A | 12/1999 | | A61C/1/14 |

* cited by examiner

*Primary Examiner*—Cary E. O'Connor
(74) *Attorney, Agent, or Firm*—Dergosits & Noah LLP

(57) ABSTRACT

A dental handpiece is disclosed, which includes a tool holder for receiving and detachably holding a dental treatment tool therein, and a tubular compressor disposed around the tool holder. The tubular compressor has a flared inner surface along a portion of its length. The tool holder and the tubular compressor are relatively slidable with respect to each other between tool holding and releasing positions. The tool holder has a plurality of integral presser tongues. Each of the presser tongues is partially separate from the tool holder with a slit to have a free tip and a connecting root with a reduced thickness. The flared inner surface of the tubular compressor elastically urges the tongues into pressure contact with the dental treatment tool to securely hold the tool in position, when the tool holder and the tubular compressor are in the tool holding position.

9 Claims, 8 Drawing Sheets

DENTAL HANDPIECE WITH TOOL HOLDER

FIELD OF THE INVENTION

The present invention relates to a dental handpiece, in particular to a dental handpiece having a tool holder for detachably holding a dental treatment tool therein.

BACKGROUND OF THE INVENTION

Dental handpieces have a tool holder for detachably holding a dental treatment tool therein. Two of such conventional dental handpieces with a tool holder are exemplified in FIGS. 6 and 8.

FIG. 6 is a sectional view of head 10 of an angle type dental handpiece having an air turbine. The head 10 accommodates rotor axis or bur sleeve 21, on which rotor 14 is fixed for rotatably driving the bur sleeve 21 by means of compressed air supplied from an external source. Coil spring 19 is introduced into the bur sleeve 21 and rests on a shoulder near the lower end opening 21a of the bur sleeve 21. Chuck member 40 is inserted into the bur sleeve 21 and contacts the upper end of the coil spring 19. There is a clearance between the inner surface of the bur sleeve 21 and the outer surface of the chuck member 40, which clearance is filled with inner tube 22 inserted from the upper end of the bur sleeve 21 and threadedly fixed on the inner surface of the bur sleeve 21. This inner tube 22 has a downwardly flared inner surface 22a in its lower end portion.

The chuck member 40 is shown in detail and partially exploded in FIG. 7. The chuck member 40 has upper tubular section 45 having a uniform outer diameter along its length, flaring section 44 having a downwardly increasing outer diameter, and annular section 41 having a uniform outer diameter. The upper tubular section 45, the flaring section 44, and the annular section 41 are formed integrally, with circumferential grooves 42 and 47 being interposed therebetween. The flaring section 44 has three axial slits 49 arranged at angular intervals. Each of these slits 49 receives a chucking die 43 of a complementary configuration.

In the bur sleeve 21, the chuck member 40 having the chucking dies 43 fitted in their corresponding slits 49, is biased upwardly by the coil spring 19, so that the outer surface of the dies 43 are contacted with the flared surface 22a. This flared surface 22a presses the dies 43 radially inwardly, so that the dies 43 press the periphery of a dental treatment tool 50 in the bur sleeve to hold the tool 50 in position.

In manufacturing the dental handpiece of the above structure, predetermined portions of the chucking member 40 should be cut away for forming the slits 49, and the corresponding dies 43 should be produced separately from the chucking member 40. Thus the dental handpiece of this type requires additional labor in producing separate parts and troublesome stock control of various parts. In assembling, this handpiece also requires additional labor in positioning the tiny dies 43 in the corresponding slits 49.

A chucking system including separate chucking dies fitted in corresponding slits in a chucking member to hold a dental treatment tool with these dies, is also disclosed in U.S. Pat. No. 4,595,363 assigned to the applicant of the present application.

FIG. 8 is a sectional view of a conventional dental handpiece of a straight type, wherein spindle 72 having coupling 84 at its proximal end is rotatably driven via the coupling 84 by means of a motor unit (not shown). The spindle 72 has an axial bore 72a in its distal portion for receiving dental treatment tool 90 therein. A plurality of apertures 72e communicating with the bore 72a are formed through the spindle 72 at angular intervals, and receive radially slidable pins 87 therein. A tubular member 75 is fitted around the spindle 72 slidably in the axial direction, and is distally biased by coil spring 78. The tubular member 75 has flared inner surface 75a in its distal portion for contact with the pins 87.

With this structure, since the tubular member 75 is distally biased by the spring 78, the flared surface 75a is brought into contact with the pins 75a in the spindle 72 to press the pins radially inwardly, so that the dental treatment tool 90 in the spindle 72 is held in position with these pins 75.

The dental handpiece of this type requires, however, production of separate tinypins 87, formation of apertures 72e, assembling of these parts, and stock control of various parts, which adds complexity and labor, as with the case of the handpiece of FIGS. 6 and 7.

SUMMARY OF THE INVENTION

The present invention aims to solve these problems in the prior art handpieces. It is therefore an object of the present invention to provide a dental handpiece, the number of which parts are minimized to eliminate problems in parts production and stock control. It is also an object of the present invention to provide a dental handpiece of which assembly is simplified compared to the prior art handpieces.

According to the present invention, there is provided a dental handpiece comprising:
   a tool holder for receiving and detachably holding a dental treatment tool therein; and
   a tubular compressor disposed around said tool holder, said tubular compressor having a flared inner surface along a portion of its length;
   said tool holder and said tubular compressor being relatively slidable with respect to each other between a tool holding position and a tool releasing position,
   wherein said tool holder has a plurality of presser tongues formed integrally with said tool holder, each of said presser tongues being partially separate from said tool holder with a slit to have a free tip and a connecting root with a reduced thickness,
   wherein said flared inner surface of said tubular compressor elastically urges said tongues into pressure contact with said dental treatment tool to securely hold the tool in position, when said tool holder and said tubular compressor are in said tool holding position.

In the dental handpiece of the above structure, the presser tongues for securely holding a dental treatment tool in position are formed integrally with the tool holder simply by providing slits and reducing the thickness of the connecting root of the presser tongues. These presser tongues are elastically urged by the flared inner surface of the tubular compressor into pressure contact with the dental treatment tool, when the tool holder and the tubular compressor are in the tool holding position, to thereby securely hold the dental treatment tool in position. Thus no tiny dies or pins are required to be produced separately from the tool holder, and accordingly no assembling step of the dies or pins and the tool holder is needed. This remarkably simplifies production, stock control, and assembly of the parts, compared to the conventional dental handpiece.

In the tool holder of the above handpiece, the presser tongues may have a flared outer surface for snugly contacting with the flared inner surface of the tubular compressor.

The slits which partially separate the presser tongues from the tool holder may be of a U-shape. The tips of the presser tongues formed by the slits may be oriented in the direction of insertion of a dental treatment tool into the tool holder in use.

The tool holder may have a plurality of connecting portions also formed integrally with the tool holder, and positioned between the presser tongues in an alternate arrangement, and the outer surfaces of the connecting portions may be offset radially inwardly from the outer surfaces of the presser tongues, so that the connecting portions do not contact with the flared inner surface of the tubular compressor.

The tubular compressor may be made stationary, while the tool holder may be made slidable with respect to the tubular compressor. Alternatively, the tool holder may be made stationary, while the tubular compressor may be made slidable with respect to the tool holder.

In the former embodiment, the handpiece may have a spring for biasing the tool holder into the tool holding position, and a push button for contacting and sliding the tool holder into the tool releasing position against the biasing force of the spring, when the push button is pressed. In the latter embodiment, the handpiece may have a spring for biasing the tubular compressor into the tool holding position, and slidable releasing means for sliding the tubular compressor into the tool releasing position against the biasing force of the spring when the slidable releasing means is slid.

According to one embodiment of the present invention, the tubular compressor may be a bur sleeve having a flared inner surface along a portion of its length, or alternatively, having a tubular member with a flared inner surface along a portion of its length, fixed, for example by threaded fitting, on the inner surface of the bur sleeve. The tool holder may be a chuck slidably positioned in the bur sleeve. The bur sleeve may have a rotor fixed on its periphery for rotatably driving the but sleeve by means of compressed air, and may be rotatably supported by upper and lower ball bearings above and below the rotor.

According to another embodiment of the present invention, the tool holder may be a spindle connected to a coupling at its proximal end for receiving rotatable driving force from a motor unit, and may be rotatably supported by a ball bearing. The tubular compressor may be a slidable tube fitted on a part of the spindle slidably in the axial direction.

BRIEF DESCRIPTION OF THE DRAWINGS

By way of example, preferred embodiments of the present invention will now be described with reference to the accompanying drawings, in which.

PREFERRED EMBODIMENT OF THE INVENTION

Figure 1:
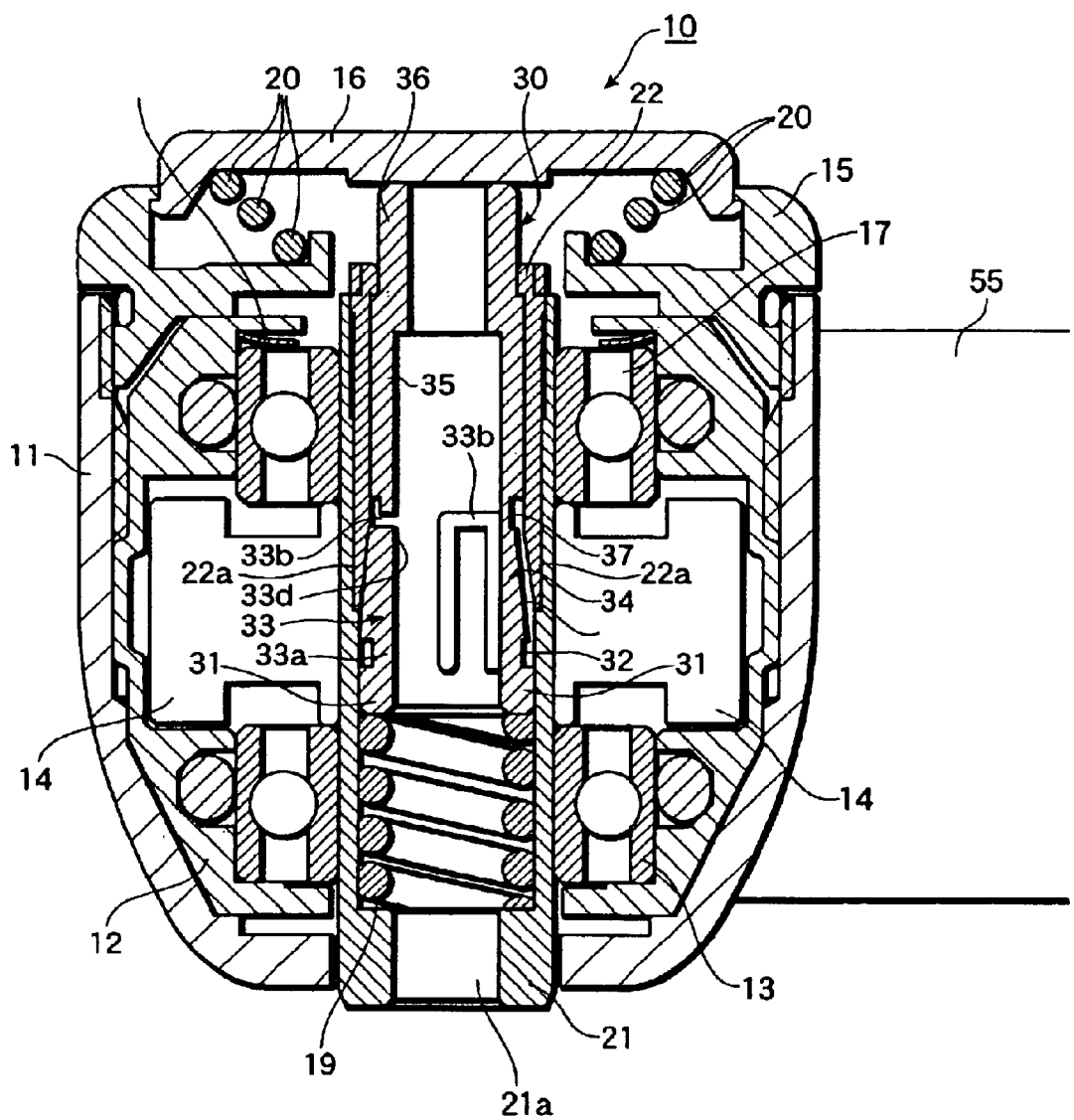
FIG. 1 is a sectional view of a head of an embodiment of a dental handpiece according to the present invention.
Figure 2:
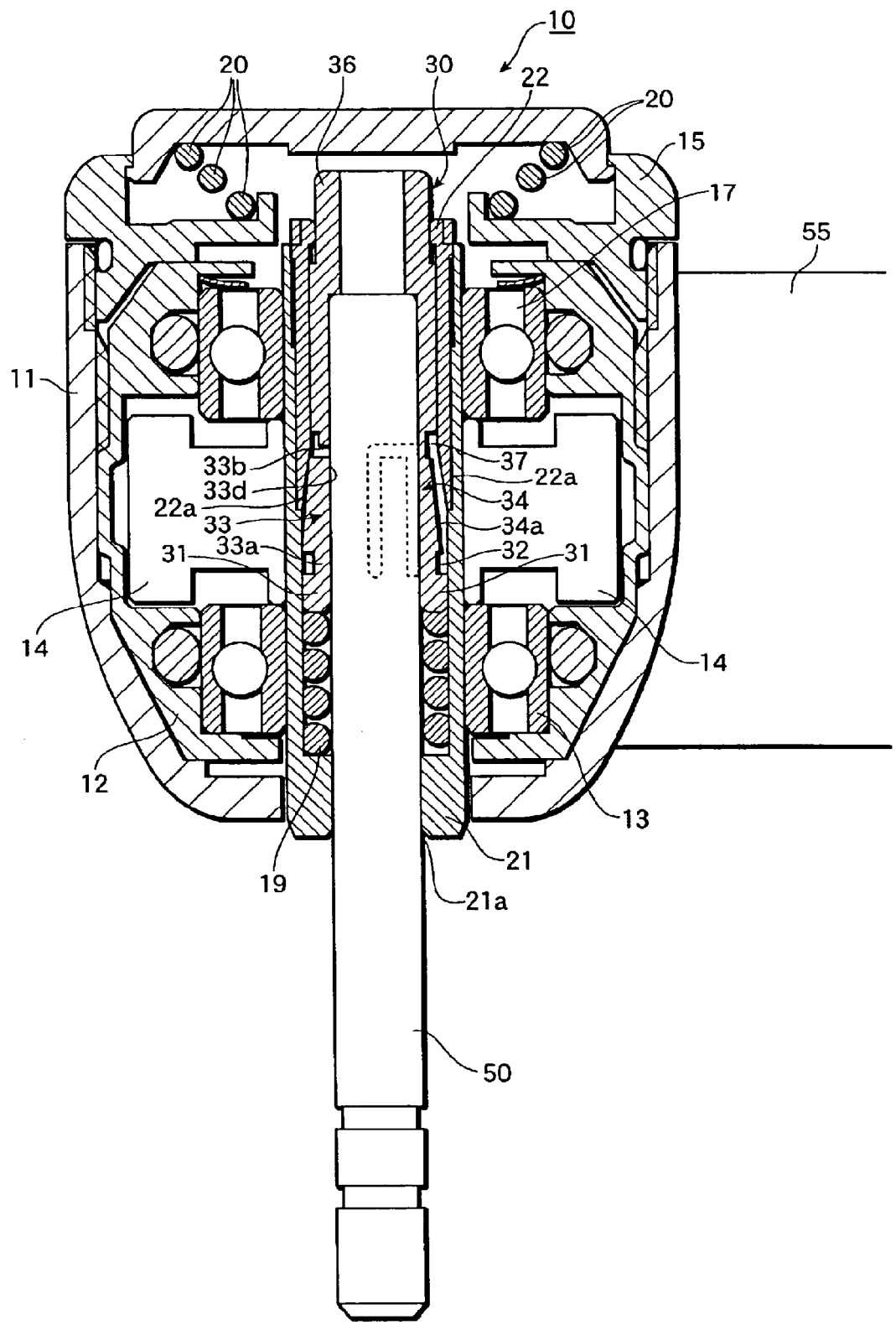
FIG. 2 is a sectional view similar to FIG. 1, with a dental treatment tool inserted.

Referring to FIGS. 1 and 2, the dental handpiece according to the present invention has head 10 on the distal end of neck portion 55 of a grip section (not shown). The head 10 includes head housing 11, in which a cartridge casing 12 is placed and secured in position with head cap 15 threadedly engaging the housing 11. The head cap 15 is provided with push button 16 biased upwardly with spring 20.

The casing 12 accommodates a rotor axis or bur sleeve 21 for receiving dental treatment tool 50 (FIG. 2) therein. The bur sleeve 21 has rotor 14 fixed on its peripheral surface for rotatably driving the bur sleeve 21 by means of compressed air supplied through an air supply passage (not shown) and discharged through an air discharge passage (not shown), which passages are provided through the neck portion 55 and the grip section and connected to an external source. Upper and lower ball bearings 17, 13 are provided above and below the rotor 14 for rotatably supporting the bur sleeve 21.

The bur sleeve 21 has an annular shoulder near tool insertion port or lower end opening 21a thereof, and coil spring 19 rests on the shoulder. Chuck member 30 for receiving and releasably holding the dental treatment tool 50 is located coaxially in the bur sleeve 21, and mounted in contact with the upper end of the coil 19. Since the chuck member 30 has a smaller outer diameter in its upper portion as will be discussed later, there is an annular clearance between the outer surface of the chuck member 30 in its upper portion and the inner surface of the bur sleeve 21. This clearance is filled with inner tube 22 inserted from the upper end of the bur sleeve 21 and threadedly fixed on the inner surface of the bur sleeve 21 to form a part of the bur sleeve 21. The inner surface of the tube 22 is flared downwardly in the lower end portion to form flared surface 22a. It should be noted that the chuck member 30 is still slidable in the bur sleeve 21 even after the clearance is filled with the inner tube 22.

Figure 3:
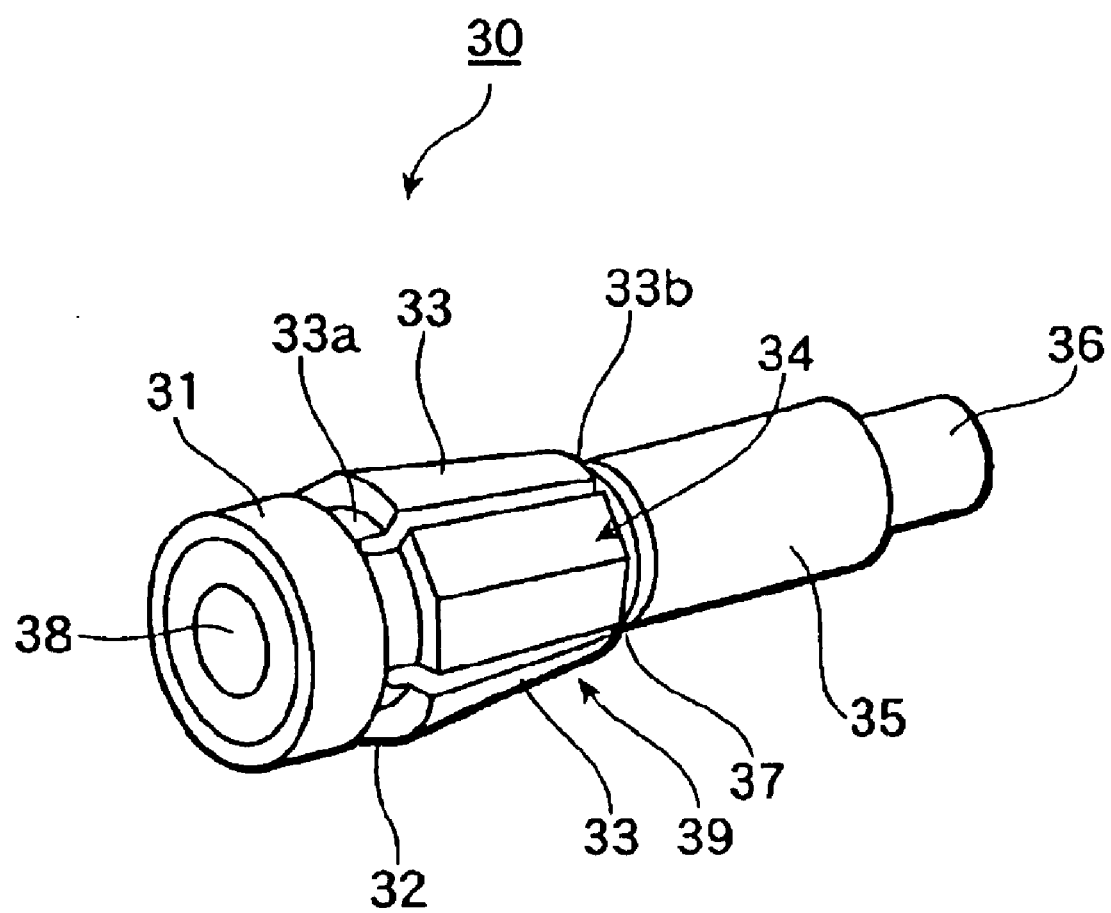
FIG. 3 is a perspective view of a chuck member of the handpiece of FIGS. 1 and 2.

Referring also to FIG. 3, the chuck member 30 has tubular section 35 having a uniform outer diameter along its length, upper end section 36 having a smaller outer diameter and integrally formed with the tubular section 35, flared section 39 having a downwardly flared outer surface, and annular section 31 connected below the flared section 39. The tubular section 35, flared section 39, and annular section 31 are integrally formed, with circumferential groove 37 being interposed between the sections 35 and 39, and circumferential groove 32 between the sections 39 and 31.

The flared section 39 includes a plurality of presser tongues 33 and a plurality of connecting portions 34 arranged alternately in the circumferential direction. Each of the presser tongues 33 is separated from the tubular section 35 and the connecting portions 34 on both sides by an inverted U-shaped slit 33b to have a free tip (FIG. 1) oriented in the direction of insertion of the tool 50, but is integrally connected to the annular section 31 via root portion 33a forming a part of the circumferential groove 32. Thus, the thickness of the root portion 33a is reduced from the outer surface. The outer surface of the presser tongues 33 is downwardly flared for snugly contacting with the flared surface 22a of the tube 22.

Each of the connecting portions 34 is separated from the adjacent presser tongues by the slits 33b on both sides, and the upper and lower ends of the connecting portion 34 form a part of the circumferential grooves 37 and 32, respectively. Thus, the connecting portions 34 are not separated from the tubular section 35 and the annular section 31, but are formed integrally with these sections via the grooves 32 and 37.

The connecting portions 34 have been formed by cutting away a predetermined thickness of the material from the outer surface so that the outer surface of the connecting portions 32 is offset radially inwardly from the outer surface of the presser tongues 33. Thus, the connecting portions 34 do not contact with the flared surface 22a of the tube 22, and form gaps between the outer surface of the connecting portions 34 and the flared surface 22a.

Operation of the dental handpiece shown in FIGS. 1 to 3 is now described. FIG. 1 shows the initial state of the handpiece before the dental treatment tool 50 is inserted into the chuck member 30. In the bur sleeve 21, the chuck member 30 is constantly biased upwards by the spring 19, so that the outer surface of the presser tongues 33 is in contact with the flared surface 22a of the tube 22, and elastically urged radially inwardly. Here, each of the presser tongues 33 is flexed radially inwardly with the root portion 33a acting as a fulcrum.

When the push button 16 is pushed down against the biasing force of the spring 20, the inner surface of the push button contacts the upper end surface 36 of the chuck member 30, and slides the chuck member 30 downwards in the bur sleeve 21 and the tube 22 against the biasing force of the spring 19. This downward slide releases the presser tongues 33 from the engagement with the flared surface 22a to locate the chuck member 30 into the tool releasing position. Here, the inner diameter of the presser tongues 33 is slightly enlarged elastically.

Then the dental treatment tool 50 is inserted into the bur sleeve 21 and the chuck member 30 beyond the presser tongues 33, and the pressure on the push button 16 is released. This causes the chuck member 30 to be biased upwards again by the spring 19, so that the outer surface of the presser tongues 33 is brought into contact with the flared surface 22a of the tube 22, and elastically urged radially inwardly. In this tool holding position, the inner surface of the tips 33d of the presser tongues 33 are in pressure contact with the periphery of the tool 50 as shown in FIG. 2, to securely hold the tool with the presser tongues 33 so as not to be drawn out while the tool is being rotatably driven.

On the other hand, since the outer surface of the connecting portions 34 is radially inwardly offset from the outer surface of the presser tongues 33, gaps are formed between the outer surface of the connecting portions and the flared surface 22a, and the flared surface 22a does not contact the connecting portions 34. This further facilitates effective pressing of the presser tongues 33 by the flared surface 22a into pressure contact with the tool 50.

Figure 4:
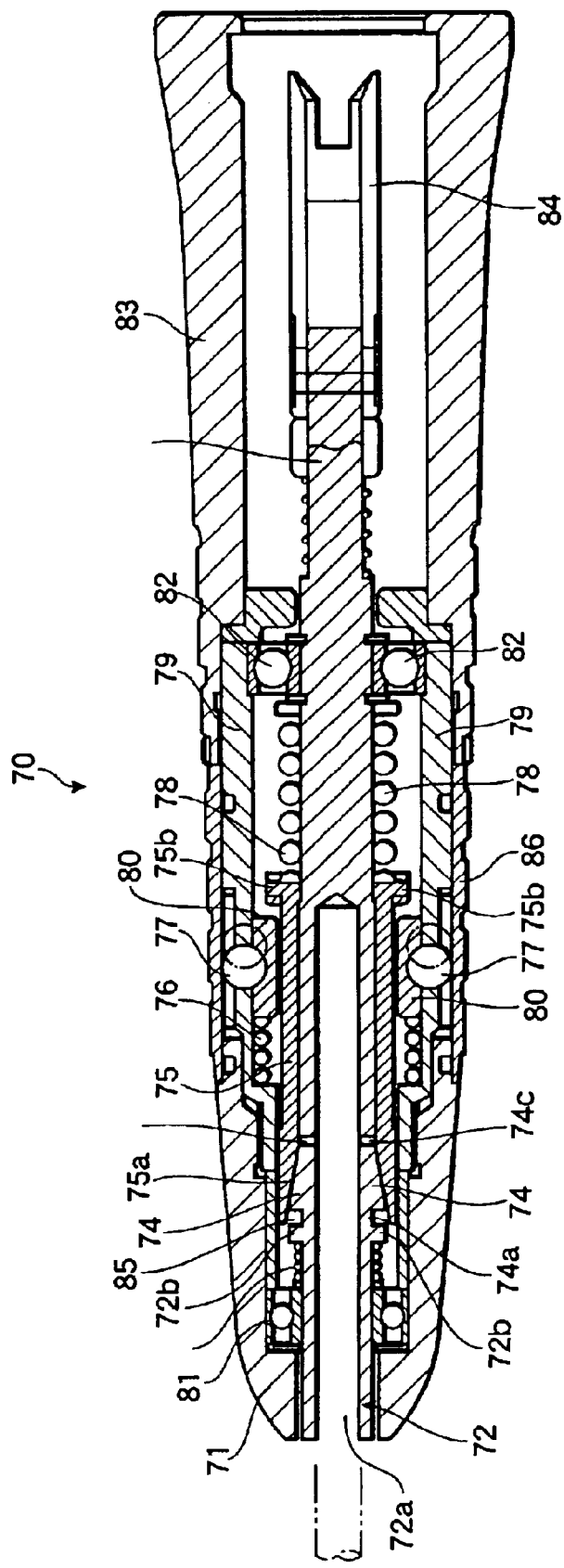
FIG. 4 is a sectional view of another embodiment of a dental handpiece according to the present invention.
Figure 5:
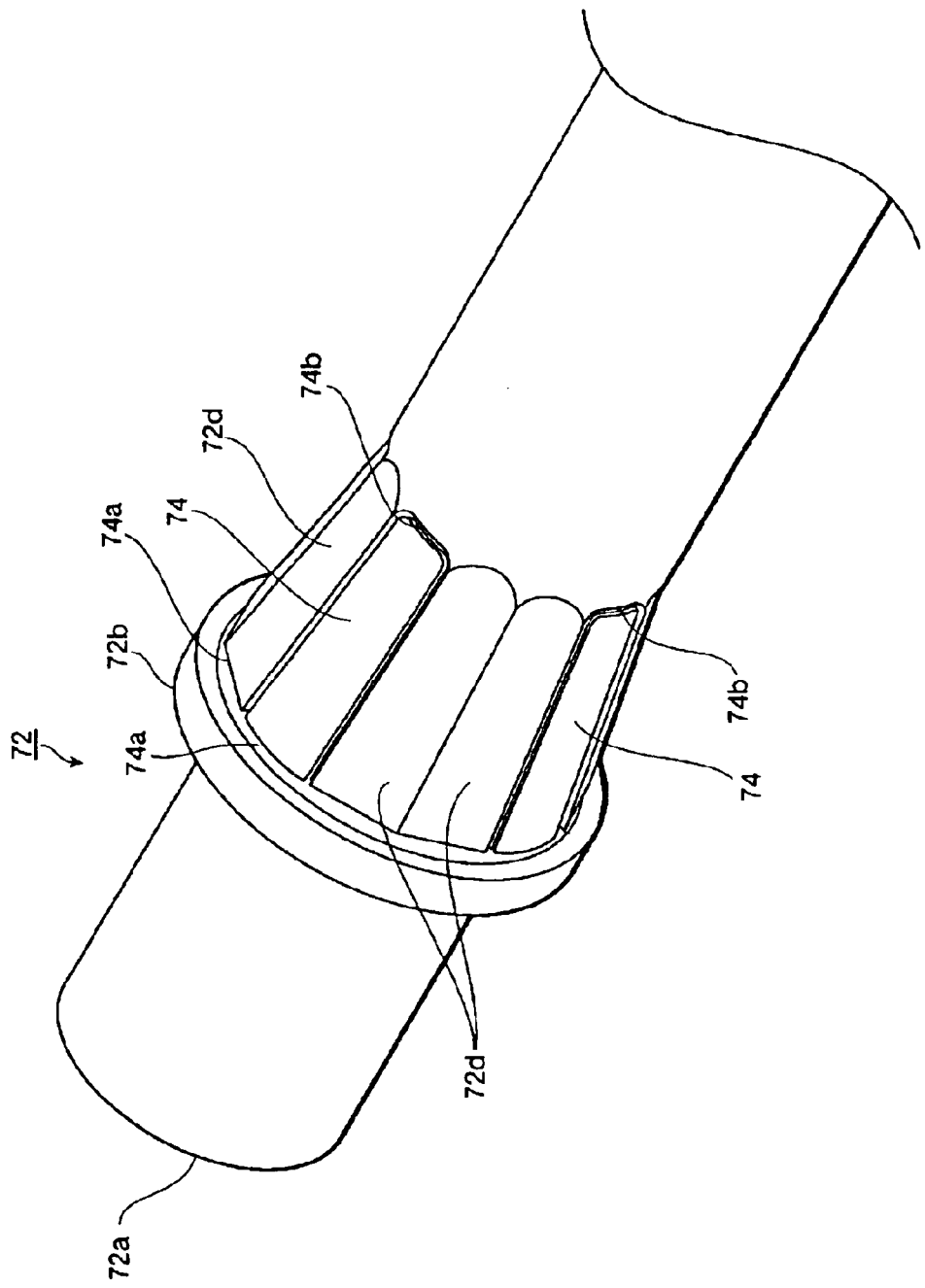
FIG. 5 is an enlarged partial perspective view of a spindle of the handpiece of FIG. 4.
Figure 6:
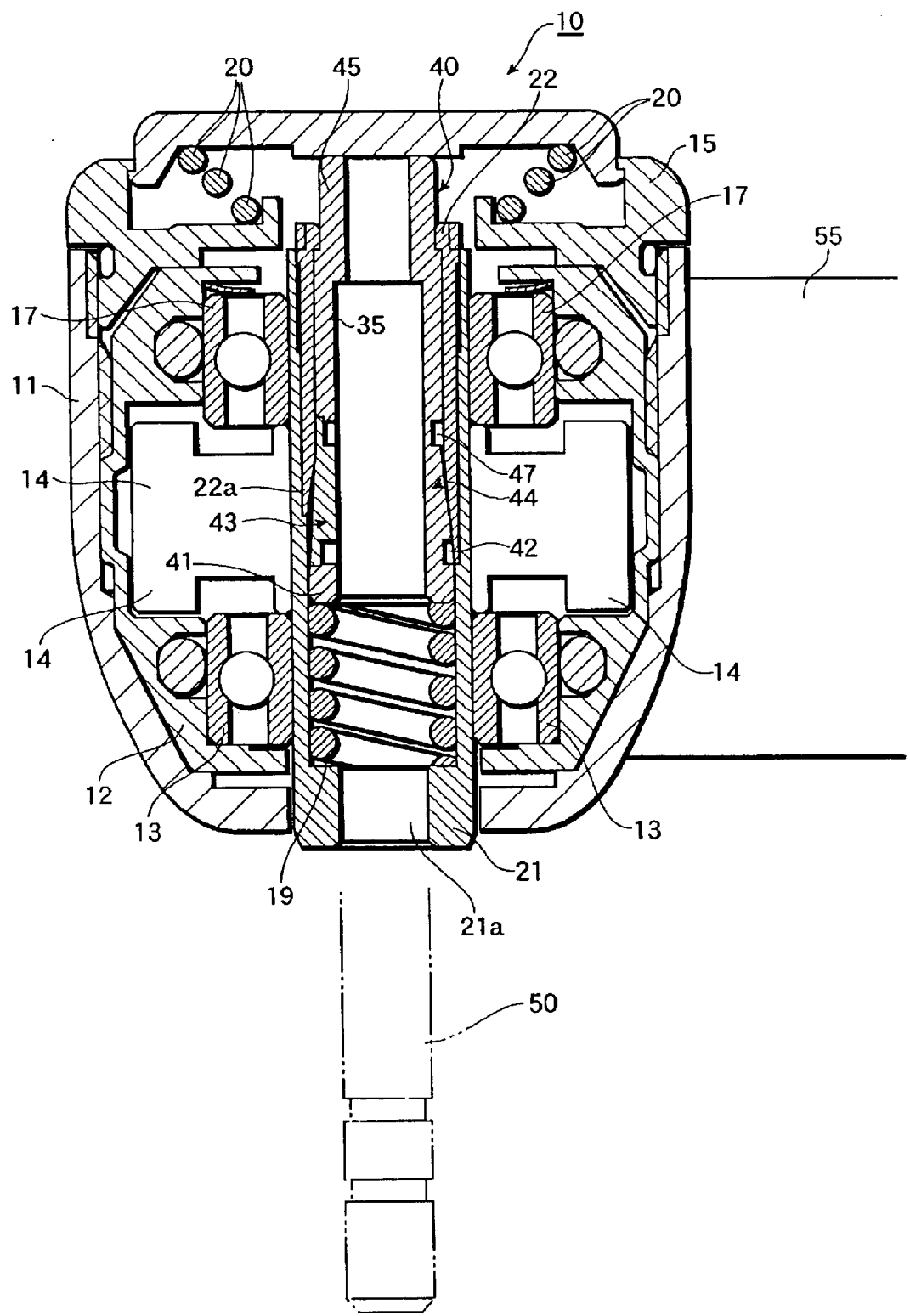
FIG. 6 is a sectional view of a head of a conventional dental handpiece.
Figure 7:
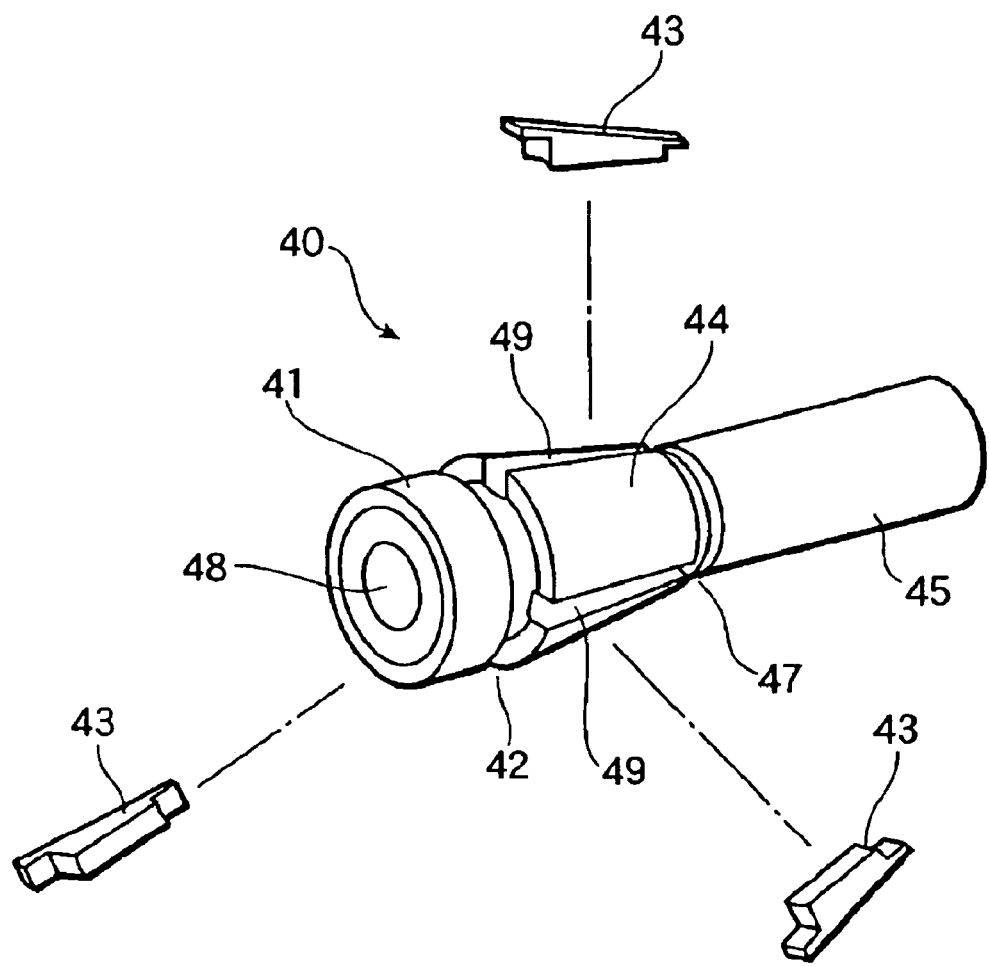
FIG. 7 is perspective view of a chuck member of the conventional handpiece of FIG. 6.
Figure 8:
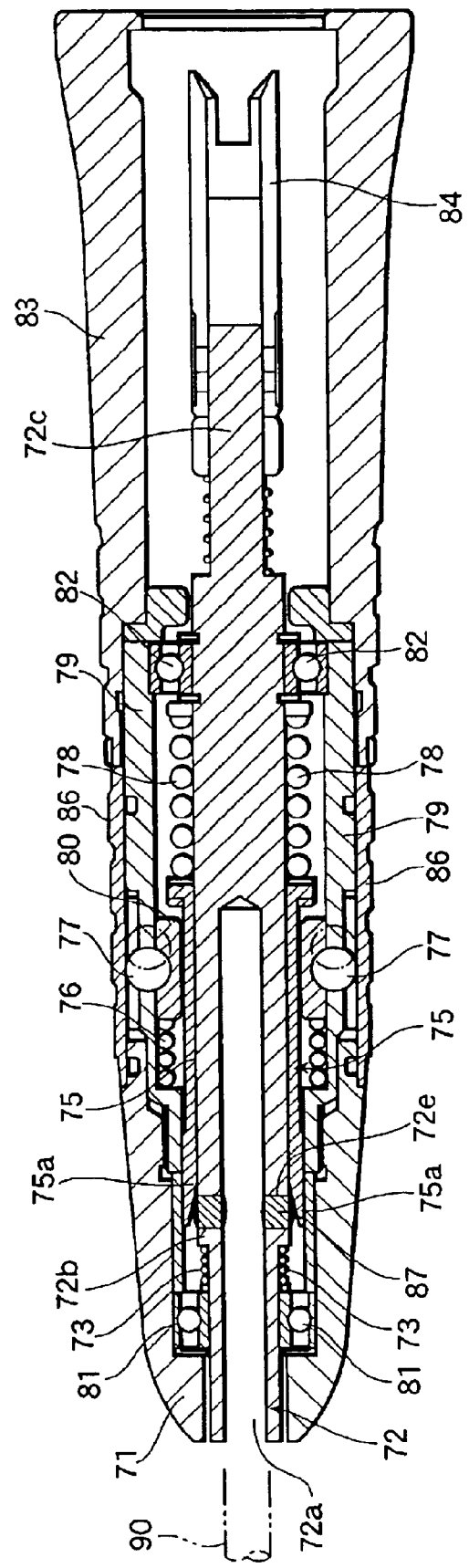
FIG. 8 is a sectional view of another conventional dental handpiece.

Referring now to FIGS. 4 and 5, another embodiment of the dental handpiece of the present invention is described. FIG. 4 shows dental handpiece 70 in a sectional view, and FIG. 5 shows a portion of the spindle of the handpiece 70 in an enlarged, perspective view.

The dental handpiece 70 includes front casing 71, sheath 79, tool detaching ring 86, and rear joint 83. Through these outer structures, spindle 72 is provided having axial bore 72a in the distal portion thereof for receiving and detachably holding dental treatment tool 90 therein. The proximal end of the spindle 72 is connected to coupling 84 located in the rear joint 83, which coupling 84 is connected to a motor unit (not shown) and transmits driving force from the motor unit to rotatably drive the spindle 72. Ball bearings 81 and 82 are provided for rotatably supporting the spindle 72.

The tool detaching ring 86 has axial grooves on its inner surface for guiding balls 77, and is rotatable in the circumferential direction. The sheath 79 positioned inside the tool detaching ring 86 has spiral slits for guiding the balls 77. Slidable ring 80 having a circumferential groove on its outer surface rotatably receives the balls 77 in the groove, and is proximally biased by coil spring 76.

Slidable tube 75 is fitted around a portion of the spindle 72 axially slidably with respect to the spindle 72. The slidable tube 75 has an annular flange 75b on its proximal end, and distally flared inner surface 75a in its distal end portion, which forms flared surface 75a. Coil spring 78 is provided abutting the proximal surface of the annular flange 75b to constantly bias the slidable tube 75 in the distal direction. The distal surface of the flange 75b is adapted such that the proximal end surface of the slidable ring 80 is brought into contact with the distal surface of the flange 75b and presses to slide the slidable tube 75 in the proximal direction, as will be discussed later.

Referring also to FIG. 5, the spindle 72 includes along its length a tubular section having a uniform outer diameter along its length, a flared section having a distally increasing outer diameter, circumferential groove 85 positioned distal to the flared section and having a reduced outer diameter, and annular flange 72b positioned distal to the groove 85. The tubular section, flared section, and annular flange 72b are integrally formed, with the circumferential groove 85 being interposed between the flared section and the annular flange 72b.

The flared section includes a plurality of presser tongues 74 and a plurality of connecting portions 72d arranged alternately in the circumferential direction. Each of the presser tongues 74 is separated from the tubular section and the connecting portions 72d on both sides by a U-shaped slit 74b to have a free tip oriented in the direction of insertion of the tool, but is integrally connected to the annular flange 72b via root portion 74a forming a part of the circumferential groove 85. Thus, the thickness of the root portion 74a is reduced from the outer surface. The outer surface of the presser tongues 74 is distally flared for snugly contacting with the flared surface 75a of the sliding tube 75.

Each of the connecting portions 72d is separated from the adjacent presser tongues 74 by the slit 74b on both sides. The upper end of the connecting portion 72d is integral with the tubular section, and the lower end of the connecting portion 72d, that is the thinned root portion 74a, forms a part of the circumferential groove 85. Thus the connecting portions 72d are not separated from the annular flange 72d, but are formed integrally with this flange via the groove 85.

The connecting portions 72d have been formed by cutting away a predetermined thickness of the material from the outer surface so that the outer surface of the connecting portions 72d is offset radially inwardly from the outer surface of the presser tongues 74. Thus, the connecting portions 72d do not contact with the flared surface 75a of the slidable tube 75, and form gaps between the outer surface of the connecting portions 72d and the flared surface 75a.

Operation of the dental handpiece 70 shown in FIGS. 4 and 5 are now described. When the dental treatment tool is not in the spindle 72 in the initial state as shown in FIG. 4, the slidable tube 75 is distally biased by the spring 78, so that the flared surface 75a of the slidable tube 75 is in contact with the outer surface of the presser tongues 74 to elastically urge the presser tongues 74 radially inwardly. Here, each of the presser tongues 74 is flexed radially inwardly with the root portion 74a acting as a fulcrum.

When the tool detaching ring 86 is rotated in the predetermined circumferential direction, the balls 77 travel in and along the spiral slits in the sheath 79, and also in and along the axial groove on the inner surface of the tool detaching ring 86 in the proximal direction. This movement of the balls 77, with the aid of the proximally biasing spring 76, causes the slidable ring 80 to move proximally to abut the distal end surface of the flange 75*b*, and further press this surface to slide the sliding tube 75 proximally relative to the spindle 72 against the biasing force of the spring 78. This proximal sliding movement of the slidable tube 75 releases the flared surface 75*a* from the engagement with the presser tongues 74 to locate the slidable tube 75 into the tool releasing position. Here, the inner diameter of the presser tongues 74 is slightly enlarged elastically.

Then a dental treatment tool is inserted into the spindle 72 beyond the presser tongues 74, and the tool detaching ring 86 is rotated in the reverse direction. This causes the balls 77 to move the slidable ring 80 distally, which in turn causes the slidable tube 75 to slid distally by the biasing force of the spring 78 into the tool holding position. When the sliding tube 75 is slid distally, the flared surface 75*a* of the sliding tube 75 is brought into contact with the outer surface of the presser tongues 74 of the spindle 72, and elastically urge the tongues 74 radially inwardly. In this tool holding position, the inner surface of the tip of the presser tongues 74 are in pressure contact with the periphery of the dental treatment tool to securely hold the tool in position so as not to be drawn out while the tool is being rotatably driven.

With the structure described above, a plurality of presser tongues are formed integrally with the tool holder, such as a chuck member or a spindle, and a flared surface is provided on the tubular compressor, such as a bur sleeve or a sliding tube, for pressing the presser tongues radially inwardly into pressure contact with a dental treatment tool held in the tool holder, when the tool holder and the tubular compressor are in the tool holding position. Thus no tiny dies or pins are required to be produced in a separate production step from the tool holder as is the case with the conventional handpiece, and thus assembly of such dies or pins and the tool holder is eliminated. Consequently, the present invention is advantageous over the conventional handpiece in that the production, stock control, and assembly of the parts may be simplified.

Although the present invention has been described with reference to the preferred embodiment, it should be understood that various modifications and variations can be easily made by those skilled in the art without departing from the spirit of the invention. Accordingly, the foregoing disclosure should be interpreted as illustrative only and is not to be interpreted in a limiting sense. The present invention is limited only by the scope of the following claims.

What is claimed is:

1. A dental handpiece comprising:

a tool holder for receiving and detachably holding a dental treatment tool therein; and a tubular compressor disposed around said tool holder, said tubular compressor having a flared inner surface along a portion of its length;

said tool holder and said tubular compressor being relatively slidable with respect to each other between a tool holding position and a tool releasing position, wherein said tool holder has a plurality of presser tongues formed integrally with said tool holder, each of said presser tongues being partially separate from said tool holder with a slit to have a free tip and a connecting root with a reduced thickness, wherein said slit is of a U-shape, and said tips of said presser tongues are oriented in a direction of insertion of said dental treatment tool into said tool holder in use, wherein said flared inner surface of said tubular compressor elastically urges said tongues into pressure contact with said dental treatment tool to securely hold the tool in position, when said tool holder and said tubular compressor are in said tool holding position.

2. The dental handpiece of claim 1, wherein said presser tongues have a flared outer surface for snugly contacting with the flared inner surface of said tubular compressor.

3. The dental handpiece of claim 1, wherein said tool holder has a plurality of connecting portions formed integrally with said tool holder, and positioned between said plurality of presser tongues in an alternate arrangement, and outer surfaces of said connecting portions are offset radially inwardly from outer surface of said presser tongues.

4. The dental handpiece of claim 1, wherein said tubular compressor is stationary, and said tool holder is slidable with respect to said tubular compressor.

5. The dental handpiece of claim 4, wherein said tubular compressor comprises a bur sleeve having a flared inner surface along a portion of its length, and said tool holder comprises a chuck slidably positioned in said bur sleeve, wherein said bur sleeve has a rotor fixed on its periphery for rotatably driving the bur sleeve by means of compressed air, and is rotatably supported by upper and lower ball bearings above and below said rotor.

6. The dental handpiece of claim 4, further comprises a spring for biasing said tool holder into the tool holding position, and a push button for contacting and sliding said tool holder into said tool releasing position against biasing force of said spring, when said push button is pressed.

7. The dental handpiece of claim 1, wherein said tool holder is stationary, and said tubular compressor is slidable with respect to said tool holder.

8. The dental handpiece of claim 7, wherein said tool holder comprises a spindle, and said tubular compressor comprises a slidable tube fitted on a part of said spindle slidably in an axial direction, wherein said spindle is connected to a coupling at a proximal end thereof for receiving rotatable driving force from a motor unit, and is rotatably supported by a ball bearing.

9. The dental handpiece of claim 7, further comprises a spring for biasing said tubular compressor into the tool holding position, and slidable releasing means for sliding said tubular compressor into said tool releasing position against biasing force of said spring when said slidable releasing means is slid.

\* \* \* \* \*